(12) United States Patent
Williams et al.

(10) Patent No.: US 6,767,708 B1
(45) Date of Patent: *Jul. 27, 2004

(54) STABILIZED AQUEOUS STEROID IMMUNOASSAY STANDARDS

(75) Inventors: Gregg T. Williams, Villa Park, IL (US); Hoda I. Aboleneen, Libertyville, IL (US); William R. Groskopf, Libertyville, IL (US); Steven C. Kuemmerle, Grayslake, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/569,886

(22) Filed: Dec. 8, 1995

Related U.S. Application Data

(63) Continuation of application No. 08/345,181, filed on Nov. 28, 1994, now abandoned.

(51) Int. Cl.$^7$ ............................................. G01N 31/531
(52) U.S. Cl. ...................... 435/7.1; 435/7.93; 435/963; 435/967; 436/13; 436/817; 436/826
(58) Field of Search ................................ 436/8, 13, 16, 436/817, 826; 424/400, 85.9, 546; 252/397, 399; 435/4, 11, 7.1, 7.93, 963, 967

(56) References Cited

U.S. PATENT DOCUMENTS

| | | | | |
|---|---|---|---|---|
| 3,274,062 A | * | 9/1966 | Lou | 436/13 |
| 4,344,940 A | * | 8/1982 | Chow et al. | 424/241 |
| 4,432,964 A | * | 2/1984 | Shell et al. | 424/14 |
| 4,436,738 A | | 3/1984 | Bequette et al. | |
| 4,672,028 A | * | 6/1987 | Olson | |
| 4,701,417 A | * | 10/1987 | Portenhauser et al. | 436/13 |
| 4,707,453 A | * | 11/1987 | Wagner et al. | |
| 4,786,606 A | * | 11/1988 | Giegel et al. | |
| 4,868,139 A | * | 9/1989 | Deeg et al. | 436/13 |
| 5,047,507 A | * | 9/1991 | Buchegger et al. | |
| 5,296,377 A | * | 3/1994 | Rapkin et al. | 436/13 |
| 5,342,760 A | * | 8/1994 | Baker et al. | 435/7.92 |

OTHER PUBLICATIONS

H. Mikola et al., "Labeling of estradiol and testosterone alkyloxime derivatives with a europium chelate for time-resolved fluoroimmunoassays", *Steroids*, vol. 58, No. 7, (1993), pp. 330–334.

\* cited by examiner

*Primary Examiner*—David Saunders
(74) *Attorney, Agent, or Firm*—Regina M. Anderson

(57) ABSTRACT

Aqueous solutions of steroid compounds which have biological activity and have a tendency to oxidative degradation at temperatures between 2 and 8° C. on storage in excess of several months are stabilized by the addition of chelators. Aqueous solutions of particular interest are protein containing solutions which mimic the behavior of human bodily fluids such as serum and are therefore suitable as standards for immunoassays for steroids in such bodily fluids. Chelators of particular interest are transition metal chelators especially those which efficiently sequester iron.

19 Claims, 3 Drawing Sheets

STABILIZED AQUEOUS STEROID IMMUNOASSAY STANDARDS

This is a continuation of application(s) Ser. No. 08/345,181 filed on Nov. 28, 1994 now abandoned.

FIELD OF THE INVENTION

Biologically active steroid compounds susceptible to degradation by oxygen in aqueous protein containing media are given enhanced storage stability by the addition of transition metal chelators.

BACKGROUND OF THE INVENTION

A widely employed method of analyzing the bodily fluids of human beings for the presence or amount of both naturally occurring and synthetic biologically active compounds is by immunoassay. The interaction between the analyte of interest and an antibody which recognizes this analyte is measured. This often provides a relatively fast and inexpensive method of quantitating the amount of a given analyte. The analyte antibody reaction may be measured in a wide variety of techniques. One technique is the competitive assay in which an anti-analyte antibody is immobilized on a solid phase and then reacted with both a known amount of a labeled analyte and a sample suspected of containing analyte. The analyte in the sample then competes with the labeled antibody for binding to the immobilized antibody. The amount of label captured by immobilized antibody is then inversely proportional to the amount of analyte present in the sample.

All analytical techniques require some reference to a standard but such reference is particularly important for immunoassays. The reagents utilized in such assays include biological materials whose reactivity is not exactly reproducible but reproducible only within a given range. In addition the immunological binding between an antibody and its analyte may be influenced by subtle factors which cannot always be controlled. In this regard too rigorous attempts to obtain precise reproducibility are inconsistent with the goal of a fast and inexpensive assay.

Therefore, the practice has developed of providing one or more standards to be included with each run of an immunoassay. For instance the $IM_x$® instrument manufactured by Abbott Laboratories can analyze in excess of twenty samples per run. It is typical to include several samples having a known amount of analyte in each run to provide a measure of the variability. Such standard samples are commonly known as controls.

In addition it is also typical to provide a number of samples having known amounts of analyte in order to calibrate and from time to time recalibrate the analyzer. Such standard samples are commonly referred to as calibrators.

For both calibrators and controls it is desirable to use a diluent which displays a behavior in the assay similar to that of the bodily fluid which is to be assayed for analyte. For instance, if human serum is to be analyzed the calibrators and controls may both be diluted in appropriately treated normal human serum. Alternatively an aqueous medium having a protein content similar to serum, for instance a buffered solution of bovine serum albumin (BSA) may be used.

A class of analytes of interest, the steroids, display a tendency to degrade over time in such buffered aqueous protein containing media. This tendency has been observed in both in charcoal stripped human serum and in aqueous solutions of BSA. In this regard, human serum intended for use as a calibrator or control matrix or carrier is charcoal stripped to remove any steroid which might be present. Thus the initial steroid content can be precisely controlled by simply adding a measured amount to the stripped serum.

Thus there is a need for calibrator and control solutions for steroid immunoassays which display extended storage stability under normal field conditions. In particular there is a need for such solutions which do not degrade significantly when stored for extended periods at temperatures between about 2 and 8° C. It is particularly desirable for such solutions to be stable for in excess of six months.

BRIEF DESCRIPTION OF THE INVENTION

Biologically active steroid compounds which are susceptible to degradation by oxidation in dilute aqueous protein in containing solutions which are suitable for the standardization of immunoassays of human bodily fluids are made more storage stable by incorporating a transition metal chelator in the solution. The steroids of interest include the naturally occurring hormonal steroids such as estradiol and progesterone. The chelators of interest include the tetra and higher dentate amino acetic acid chelators such as diethylenetriamine pentaacetic acid (DETP) and ethylenediamine tetraacetic acid. The aqueous media of interest include charcoal stripped normal human serum and aqueous solutions of bovine serum albumin (BSA), especially those buffered to a pH between about 6 and 9. The solutions of particular interest include those with a steroid concentration between about $2.5 \times 10^{-11}$ and $1.0 \times 10^{-7}$ g/mL and a chelator concentration of greater than about 0.1 mM, preferable between about 0.2 and 50 mM.

DETAILED DESCRIPTION OF THE INVENTION

Figure 1:
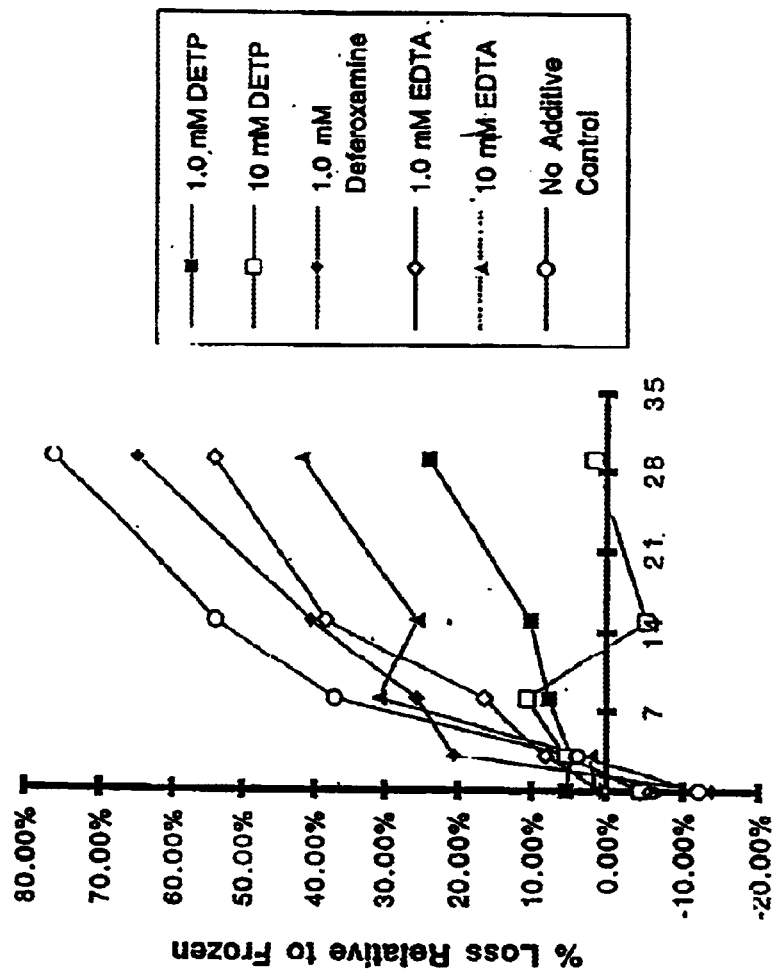
FIG. 1 is a series of plots of loss of progesterone in a standard solution versus days at 37° C. for a variety of chelators and a control specimen.

The steroids of interest with regard to the present invention are those which display biological activity in humans and have a tendency to undergo oxidative degradation in an aqueous medium. These steroids are likely targets for immunoassay and consequently are likely to be utilized as standards for such assays. Such standards typically utilize aqueous media in order to present the reference steroid to the assay in a medium similar to the bodily fluid on which the immunoassay is being conducted. Among these steroids are the naturally occurring hormonal steroids and those of particular interest are those whose normal biological levels fluctuate such as the female sex hormones. Included within this group are progesterone, estrone and estradiol. Other steroids of interest include cortisol and testosterone.

The chelating agents or chelators of interest are those that are able to sequester metal ions from an aqueous medium. Of particular interest are those chelators which are able to sequester transition metals. It is believed that the oxidative degradation of steroids in aqueous media proceeds through a transition metal catalyzed route and thus chelators which can inhibit this activity by complexing with such metals are of particular interest. Iron is believed to be a particularly important agent in such degradation reactions and consequently chelators that are particularly effective in sequestering iron are of especial interest.

Chelators of interest include the following:
2,2'-dipyridine, or bipyridine
1,2-bis(diethylphosphino)ethane
1,2-bis(diethylphosphino)methane
o-phenylenebisdimethylarsine [o-$C_6H_4(AsMe_2)_2$]
diethylenetriamine [$H_2N(CH_2CH_2NH)_2H$]
{[2,2-dimethyl-1,3-dioxolan-4,5-diyl)bis(methylene)]bis (diphenylphosphine)}
1,2-bis(diphenyl-phosphino)ethane, dppe
ethylenediaminetetraacetic acid
ethylenediamine [$H_2NCH_2CH_2NH_2$]
tris-(2-dimethylaminoethyl)amine [$N(CH_2CH_2NMe_2)_3$]
bis-(2-diphenylphosphinoethyl)amine [$HN(CH_2CH_2PPh_2)_2$]
tris-(2-diphenylphosphinoethyl)amine [$N(CH_2CH_2PPh_2)_3$]
1,10-phenanthroline
propylenediamine(1,2-diaminopropane)
bis-(2-diphenylphosphinoethyl)amine [$HN(CH_2CH_2PPh_2)_2$]
tris-(2-diphenylphosphinoethyl)phosphine [$P(CH_2CH_2PPh_2)_3$]
salicylaldehyde
bis-salicylaldehydeethylenediimine
tris-(2-diphenylarsinoethyl)amine [$N(CH_2CH_2AsPh_2)_3$]
tris-(3-dimethylarsinopropyl)phosphine [$P(CH_2CH_2CH_2AsMe_2)_3$]
bis-(3-dimethylarsinopropyl)methylarsine [$MeAs(CH_2CH_2CH_2ASMe_2)_2$]
N,N,N',N'-tetramethylethylenediamine (also TMED, tmed)
1,3-diaminopropane(trimethylenediamine)
tris-(2-diphenylphosphinoethyl)amine [$N(CH_2CH_2PPh_2)_3$]
tris-(2-aminoethyl)amine [$N(CH_2CH_2NH_2)_3$]
triethylenetetraamine [$(—CH_2NHCH_2CH_2NH_2)_2$]
tris-(2-methylthiomethyl)amine [$N(CH_2CH_2SMe)_3$]
deferoxamine [N'-[5-[[4-[[5-(Acetylhydroxyamino)pentyl] amino]-1,4-dioxobutyl]hydroxyamino]pentyl]-N-(5-aminopentyl-N-hydroxybutanediamide]

Preferred chelators include those which are tri or higher dentate, with the tetra and penta dentate being particularly preferred. Among the preferred chelators those which have an amino acetic acid structure and among these ethylenediamine tetraacetic acid and diethylenetriamine pentacetic acid are especially preferred.

The aqueous media of particular interest are those which have a substantial protein content. It is often desirable for the standards for an immunoassay to be carried in a medium which is similar to or mimics the behavior of a human bodily fluid such as a serum. In some cases it is advantageous to use protein contents dramatically different than that of the human bodily fluid to be assayed. This may allow adjustment for other characteristics of the bodily fluid. Human bodily fluids including serum have a substantial protein content. Typical protein concentrations may range between about 10 and 300 mg/mL with about 50 mg /mL being typical for serum. This protein content may be naturally present, for instance in normal human serum, or may be added such as a five percent weight per volume aqueous solution of bovine serum albumin (BSA).

It is preferred that the aqueous medium be substantially free of fibrinogen. Thus it is preferred to use media other than plasma. In this regard it is also preferred to avoid media which contain particulate forming components.

It is preferred that the protein solution be essentially free of indigenous steroid. Thus if the protein solution is normal human serum it is preferably charcoal stripped to remove the naturally occurring steroids. On the other hand, protein preparations from which the steroids have been removed by other techniques such as commercially available steroid free non-charcoal stripped BSA are especially preferred. Among these are those obtained by a wash with an organic phase. It is felt that charcoal stripping may contribute undesirable transition metals such as iron.

It is felt that the protein itself may be a source of undesirable transition metals. Proteins are known to complex with metals in ways which make it difficult to obtain transition metal free protein.

It is preferred although not necessary that the aqueous medium have a pH similar to that of human bodily fluids. It is particularly preferred that the aqueous medium have a pH between about 6 and 9 with a pH between 7 and 8.5 being especially preferred. The pH of the aqueous medium is conveniently adjusted with any of the common buffers utilized with biological materials such as tris (hydroxymethly) aminomethane commonly known as TRIS.

The steroid concentrations of the aqueous solutions of interest should span the range of steroid concentrations encountered in assaying human bodily fluids. Typically various steroids are assayed for at levels between about 5 picograms per mL and 100 nanograms per mL. Of particular interest are concentrations between about $5 \times 10^{-11}$ and $4 \times 10^{-8}$ gram per mL.

The chelators should be utilized in amounts effective to inhibit the oxidative degradation of the aqueous steroid solutions. It is preferred to utilize them in amounts in excess of about 0.1 mM and it is particularly preferred to use them in amounts between about 0.2 and 50 mM. It is, particularly advantageous to utilize a chelator concentration of at least about 1 mM. There appears to be a limited advantage in utilizing chelator concentrations in excess of about 20 mM especially with the more effective iron chelators of the amino tetra and penta acetic acid class. However, other than the cost there does not appear to be much disadvantage in using higher concentrations.

The inhibition of oxidative degradation achieved by the chelators may be conveniently assessed by stressing aqueous steroid solutions at elevated temperatures for various times and observing the loss of steroid content detectable by imunoassay. The results obtained by elevated temperature testing are predictive of the longer term stability of steroid solutions held at lower temperatures.

Steroid standards for immunoassays are typically maintained at temperatures between about 2 and 8° C. and desirably have stabilities in excess of about six months, i.e. do not display significant degradation within six months. It is particularly desirable that the standards display a loss of signal in an immunoassay of less than about 10 percent preferably less than about 5 percent.

Such stabilities can be conveniently projected from heat aging at about 37° C. over the course of between 4 and 5 weeks. Compositions which display less than about 10% loss for four weeks are expected to have stabilities in excess of about six months.

The following examples are illustrative of the invention and are in no way to be interpreted as limiting the scope of the invention, as defined in the claims. It will be appreciated that one skilled in the art can conceive of many other devices and methods of use to which the present inventive concepts can be applied.

EXAMPLE 1

IMx® Estradiol Assay

Estradiol assays were performed with the following format on IMx® disposable cartridges by an IMx® instrument.

Seventy five microliters (75 µL) of a serum sample were mixed with 35 µL of 5-α-dihydrotestosterone buffer (DHT buffer), 50 µL of a rabbit anti-estradiol antibody coated microparticle suspension and 90 µL of IMx® Buffer. The reaction mixture was incubated for 27.5 minutes at 37° C. DHT buffer was an aqueous pH 4.5 solution of 2 µg/mL of 5-α-dihydrotestosterone, 0.75% (w/v) saponin, 0.5 M glycine, 0.25 mM sodium citrate and 0.12% methyl isothiazolinone. The rabbit anti-estradiol antibody coated microparticle supension contained 0.01% solids suspended in microparticle buffer which was an aqueous pH 6.5 solution of 0.1 M bis-(2-hydroxyethyl)iminotris(hydroxymethyl) methane (Bis-Tris), 0.1 M sodium chloride, 13.6% sucrose, 0.1% sodium azide and 0.2 mg/mL normal rabbit IgG. IMx® Buffer was an aqueous pH 7.5 solution of 0.3 M NaCl, 0.1 M TRIS (tris(hydroxymethyl)aminomethane) and 0.1% sodium azide. IMx® Estradiol reagents (including DHT buffer, rabbit anti-estradiol antibody coated microparticle suspension, conjugate and methylumbelliferone phosphate substrate), IMx® Buffer, IMx® disposable cartridges, and IMx® instruments and are available commercially from Abbott Laboratories, Abbott Park, Ill. and are described in U.S. Pat. No. 5,342,760, EP-A-288 793 and in Fiore et al., Clin. Chem. 34/9:1726–1732, 1988, all of which are incorporated herein by reference.

One hundred seventy five microliters (175 µL) of the reaction mixture were transferred to the fiber matrix of an IMx® disposable cartridge. The fiber matrix is located over an absorbent pad of the IMx® cartridge. The microparticles were captured by the fiber matrix and the solution was absorbed by the absorbent pad. The microparticles were then washed with IMx® Buffer. Sixty microliters (60 µL) of estrone 6-(O-carboxymethyl)oxime alkaline phosphatase conjugate solution were added to the matrix, incubated for 12 seconds at 37° C., and then washed again with IMx® Buffer. The conjugate solution was an aqueous pH 6.5 solution of 0.1 M Bis-Tris, 0.5 M sodium chloride, 1% casein, 1 mM magnesium chloride, 0.1 mM zinc chloride and 0.1% azide containing sufficient conjugate to give a certain signal strength when utilized in an assay of sample free of analyte.

Sixty-five microliters (65 µL) of an aqueous pH 9 solution of 1.2 mM 4-methylumbelliferone phosphate and 0.1 M 2-amino-2-methyl-1-propanol were added to the matrix and the rate of 4 methylumbelliferone formation was measured by fluorescence reflectance. The IMx® instrument measured fluorescence with a fluorometer that used a mercury arc lamp as its light source (as described in Fiore et al., Clin. Chem. 34/9:1726–1732, 1988, the contents of which are incorporated herein by reference). Using calibrators containing 0, 50, 250, 750, 1500, and 3000 pg/mL of estradiol a standard curve was constructed. Using this curve this assay was determined to have a mean sensitivity of 13.9±4.3 pg/mL.

EXAMPLE 2

IMx® Progesterone Assay

Progesterone assays were performed on IMx® disposable cartridges by an IMx® instrument using a format similar to the estradiol assay in Example 1, with the following modifications. Fifteen microliters (15 µL) of a serum sample were mixed with 80 µL of progesterone sample buffer, 80 µL of an anti-progesterone antibody coated microparticle suspension and 75 µL of IMx® Buffer. The reaction mixture was incubated for 20.8 minutes at 37° C. Progesterone sample buffer was an aqueous pH 2.8 solution of 2.25 M glycine, 0.5 µg/mL of 5-α-dihydrotestosterone, 0.2% (w/v) saponin, 0.1 M sodium chloride and 0.1% methyl isothiazolinone (available from Rohm and Haas, Philadelphia, Pa.). The anti-progesterone antibody (available from University of Surry, Australia) coated microparticle suspension contained 0.001% solids (microparticles available from Seradyne, Indianapolis, Ind.) suspended in a buffer that was a pH 6.5 aqueous solution of 0.5 M morpholinoethanesulphonic acid (MES), 0.1 M sodium chloride, 10% sucrose, 2% bovine serum albumin (available from Intergen, Hawthorne, N.Y.), 0.1 mg/mL sheep IgG (50% ammonium sulfate cut of sheep serum obtained from Irvine Scientific, Santa Ana, Calif.) and 0.2% sodium azide.

One hundred seventy five microliters (175 µL) of the reaction mixture were transferred to the fiber matrix of an IMx® disposable cartridge. The microparticles were then washed with IMx® Buffer. Sixty microliters (60 µL) of 17-hydroxyprogesterone-3-(O-carboxymethyl)oxime alkaline phosphatase conjugate solution were added to the matrix, the reaction was incubated for 8 seconds at 37° C., and then washed again with IMx® Buffer. The conjugate solution contained 17-hydroxyprogesterone (available from Steraloids, Wilton, N.H.) coupled to alkaline phosphatase (available from Boehringer Mannheim, Germany) by means of the EDAC coupling procedure as described in U.S. Pat. No. 5,342,760. The conjugate solution was a pH 7.4 aqueous solution of 50 mM tris, 100 mM sodium chloride, 10 mM magnesium chloride, 0.1 mM zinc chloride, 0.5% casein (available from Sigma Chemical, St. Louis, Mo.) and 0.1% sodium azide containing sufficient conjugate to give a certain signal strength when utilized in an assay of sample free of analyte.

The addition of 4-methylumbelliferone phosphate and quantification of the rate of 4 methylumbelliferone formation was as described in Example 1. Using calibrators containing 0, 1, 4, 10, 20, and 40ng/mL of progesterone a standard curve was constructed. Using this curve this assay was determined to have a mean sensitivity of 0.13 ng/mL.

EXAMPLE 3

Preparation of Serum Matrix

Steroid stripped serum was prepared by mixing one liter of normal human serum (available from Interstate Blood Bank, Memphis, Tenn.) with 50 grams of activated charcoal (available from R. W. Greef and Co., Orland Park, Ill.). After two hours of room temperature mixing, the charcoal was removed by filtration. Alkaline shocked serum was used for estradiol serum matrices (available from Abbott Laboratories as IMx® Estradiol Specimen Diluent). Alkaline shocked serum was prepared from charcoal stripped serum by raising to pH 11 with 6N sodium hydroxide, incubating the mixture at 2–8° C. for approximately 18 hours, adjusting the pH to about 8.0 with 6N HCl and filtering the final mixture. Sodium azide was added to 0.2% (w/v) for all serum matrices. Estradiol (available from Sigma Chemical, Saint Louis, Mo.) or progesterone (available from Sigma Chemical, Saint Louis, Mo.) were added to aliquots of steroid stripped serum to generate calibrators, controls, or test samples for the stability experiments described below.

EXAMPLE 4

Preparation of BSA Matrix

A Bovine Serum Albumin (BSA) based calibrator matrix for IMx Estradiol was prepared, by dissolving BSA stripped of steroids by an organic wash (available from Miles Pentex, Kankakee, Ill.) to a concentration of 5% (w/v) in a pH 8 aqueous solution of 0.1 M tris(hydroxymethyl) aminomethane and 0.2% sodium azide.

EXAMPLE 5

Effects of Various Chelators on the Stability of Progesterone in Serum

A technique was devised that decreased the observation time required to measure steroid sample decomposition in order to obtain useful information on the stability of progesterone and estradiol calibrators and controls from matrix stability experiments in a reasonable period of time. Test samples were incubated at 37° C. and observed over a period of days or weeks. The higher temperature accelerated the steroid degradation that normally would have required observation over periods of months, had the calibrators and controls been stored at 2–8° C. the entire time.

Charcoal stripped human serum as prepared in Example 3 (non-alkaline shocked) (10 mL) was aliquoted into glass scintillation vials and various metal chelators were added to the following final concentrations:

a) 1.0 mM diethylenetriaminepentaacetic acid (DETP, available from Sigma Chemical, Saint Louis, Mo.).
b) 10.0 mM diethylenetriaminepentaacetic acid (DETP).
c) 1.0 mM ethylenediaminetetraacetic acid (EDTA, available from Sigma Chemical, Saint Louis, Mo.).
d) 10.0 mM ethylenediaminetetraacetic acid (EDTA).
e) 1.0 mM Deferoxamine mesylate (available from Sigma Chemical, Saint Louis, Mo.).

Samples were incubated on a rocker for 12 min. at room temperature and then spiked to 5 ng/mL with 10 µg/mL progesterone (available from Sigma Chemical, Saint Louis, Mo.) prepared in an ethanol stock solution. Samples were assayed for baseline concentrations of progesterone following an 8 min. incubation on a rocker at room temperature. Four 1.0 mL aliquots of each composition were placed in TDx® microcentrifuge tubes (available from Abbott Laboratories, Abbott Park, Ill.) and stored frozen –20° C. The scintillation vials were incubated at 37° C. On the days indicated, aliquots were thawed and tested with the corresponding aliquots drawn from the vials stored at 37° C. to assess percent loss.

Percent loss (% loss) is an absolute determination of the loss of progesterone in the stressed sample relative to the frozen aliquot. As many as 24 samples can be tested during a single run of the IMx® instrument. The IMx® measures the rate of 4-methylumbelliferone formation, which is proportional to the amount of steroid-alkaline phosphatase conjugate binding. Because the IMx® estradiol and progesterone assays are competitive, the rate of 4-methylumbelliferone formation is inversely proportional to analyte concentration. The comparison of concentrations for test samples from a single run, therefore, can provide a internally controlled indication of analyte concentration. Such comparisons are not complicated by between run or instrument to instrument variations.

For these experiments, unspiked aliquots were included in the same run with the spiked aliquots. Concentrations were determined for each aging condition by dividing the signal from a stressed or frozen spiked sample by the signal from the unspiked aliquot and plotting the result on a displacement curve previously developed for this assay. The per cent loss is determined by dividing the difference between the frozen and stressed concentrations by the concentration obtained for the frozen aliquot. The results are displayed as percent loss, i.e., [(Frozen-Stressed)/Frozen]×100%. FIG. 1 illustrates the reduction in % loss over time (days 0, 3, 8, 15 and 29) by the addition of Deferoxamine, DETP and EDTA compared to no added reagent. The reduction in % loss was most effective for 10 mM DETP followed by 1 mM DETP. Percent loss was eliminated with 10 mM DETP after 29 days compared to almost 80% loss with no reagent added.

EXAMPLE 6

Stabilization of Estradiol in Serum by DETP

Figure 2:
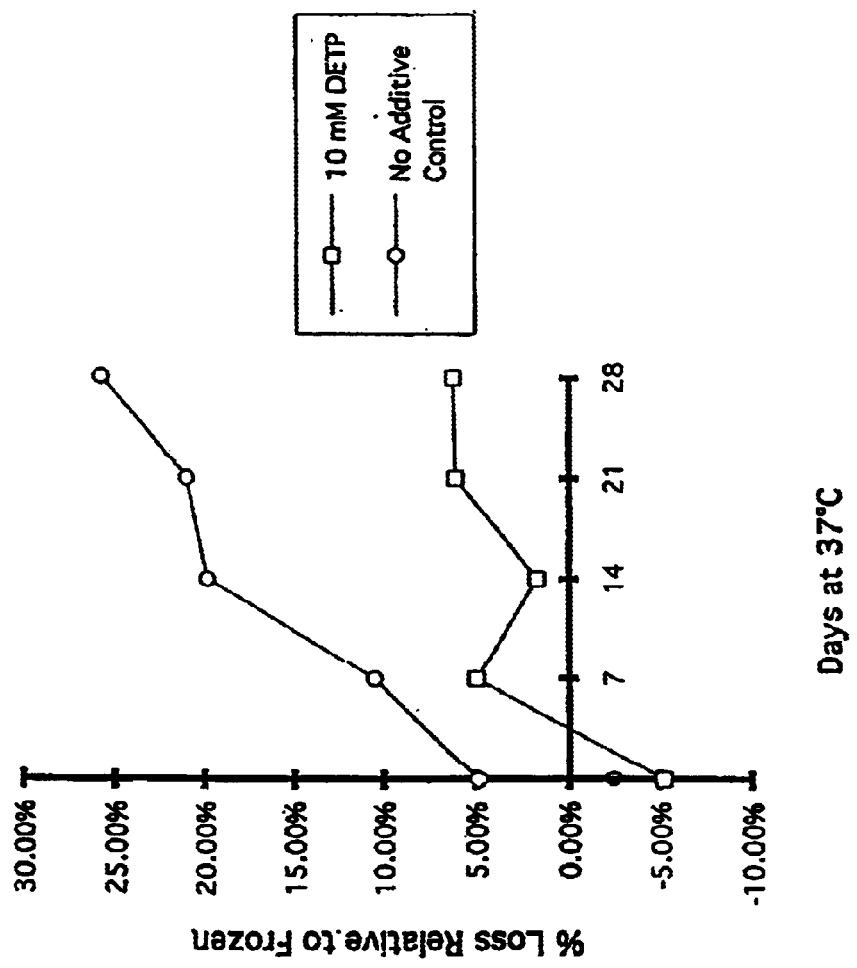
FIG. 2 is a plot of loss of estradiol in a standard solution versus days at 37° C. for a chelator and a control specimen.

Fifteen milliliters (15 mL) of alkaline shocked charcoal stripped human serum prepared in Example 3 were aliquoted into a glass scintillation vial and diethylenetriaminepentaacetic acid (DETP) was added to 10 mM. A control sample was prepared with no added DETP. The samples were incubated on a rocker for 8 min. at room temperature, allowed to equilibrate for 2 hours, and then spiked to 750 pg/mL with a 500 ng/mL estradiol (available from Sigma Chemical, Saint Louis, Mo.) stock solution prepared in charcoal stripped serum. Following a 5 min. incubation on a rocker at room temperature, samples were assayed for baseline concentrations. Four one milliliter aliquots were placed in TDx® microcentrifuge tubes (available from Abbott Laboratories, Abbott Park, Ill.) and frozen at –20° C. The scintillation vials were incubated at 37° C. On the days indicated, frozen aliquots were thawed and tested with the corresponding aliquots drawn from the vials stored at 37° C. to assess percent loss using the data treatment outlined in example 5 but assuming that the results could be normalized using the standard signal for an unspiked specimen. FIG. 2 illustrates the reduction in % loss over time (days 0, 7, 14, 21 and 28) by the addition of 10 mM DETP compared to no added reagent. Percent loss was observed to decrease from over 20% to almost no loss after 28 days by the addition of 10 mM DETP.

EXAMPLE 7

Stabilization of Estradiol in 5% BSA Matrix by DETP

Figure 3:
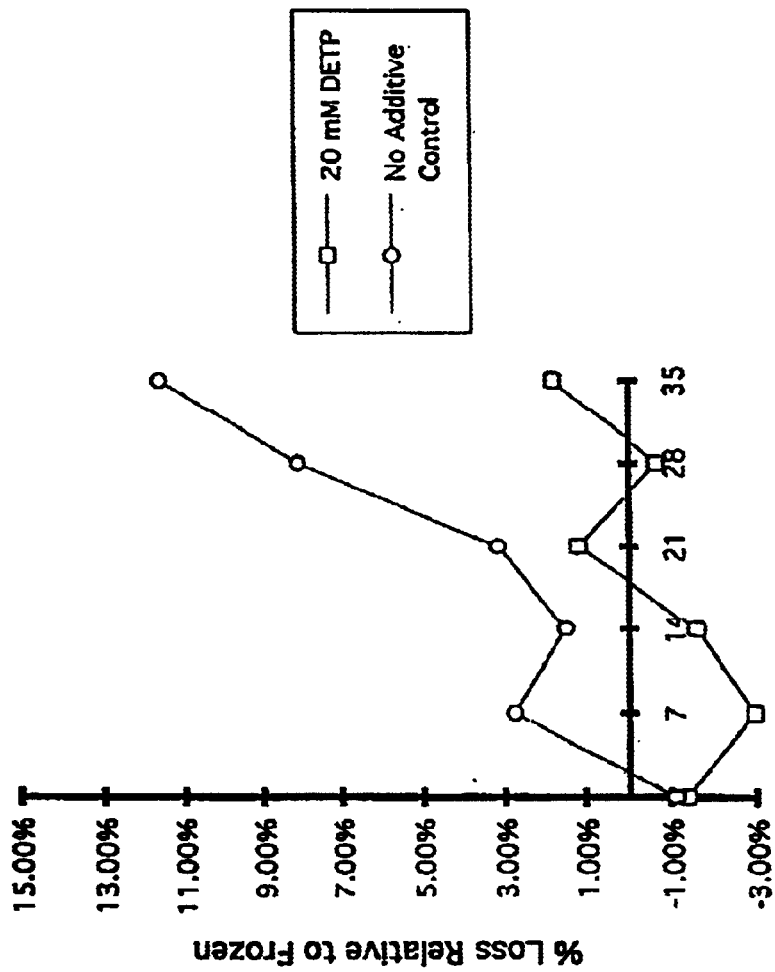
FIG. 3 is a plot of loss of estradiol in a standard solution versus days at 37° C. for a chelator and a control specimen.

A BSA sample matrix was prepared as described in Example 4 and divided into two master aliquots. DETP was added to one aliquot to 20 mM. Estradiol was added to both aliquots to a concentration of 750 pg/mL, and each aliquot was further aliquoted into 10 polyethylene dropper bottles. Five dropper bottles from each master aliquot were incubated at 37° C. and the other five were frozen at –20. On the days indicated, a frozen aliquot was thawed and tested with a corresponding 37° C. aliquot to assess percent loss as described in example 6. FIG. 3 illustrates the reduction in % loss over time (days 0, 7,1 4, 21 28 and 35) by the addition of 20 mM DETP compared to no added reagent. Percent loss was observed to decrease from over 10% to almost no loss after 28 days by the addition of 20 mM DETP.

The embodiments described and the alternative embodiments presented are intended as examples rather than limitations. Thus, the description of the invention is not intended to limit the invention to the particular embodiments disclosed, but it is intended to encompass all equivalents and subject matter within the spirit and scope of the invention as described above and as set in the following claims.

We claim:

1. A calibrator composition for use as a reference standard in an immunoassay consisting essentially of a steroid and diethylene triamine pentaacetic acid in an aqueous medium.

2. The composition of claim 1, wherein said aqueous medium is a protein containing aqueous medium.

3. An aqueous steroid calibrator solution for use as a reference standard in an immunoassay consisting essentially of:
   1) a steroid compound capable of undergoing transition metal catalyzed oxidative degradation in an aqueous medium;
   2) diethylenetriamine pentaacetic acid; and
   3) a protein.

4. The composition of claim 3 wherein said steroid is present in a concentration between about $2.5 \times 10^{-11}$ and $1.0 \times 10^{-7}$ g/ml.

5. The composition of claim 3, wherein said diethylenetriamine pentaacetic acid is present in a concentration of greater than about 0.1 mM.

6. The composition of claim 5 wherein said diethylenetriamine pentaacetic acid is present in a concentration between about 0.2 and 50 mM.

7. A steroid containing aqueous calibrator solution for use as reference standard in an immunoassay consisting essentially of:
   1) a steroid compound capable of undergoing transition metal catalyzed oxidative degradation in an aqueous medium;
   2) diethylenetriamine pentaacetic acid; and
   3) a protein in a range between about 10 mg/mL to 300 mg/mL.

8. The composition of claim 7, wherein said solution is buffered.

9. The composition of claim 7 wherein said protein is bovine serum albumin.

10. The composition of claim 7 wherein the protein is charcoal stripped normal human serum.

11. The composition of claim 7 wherein said steroid compound is estradiol or progesterone.

12. The composition of claim 11 wherein the steroid compound is estradiol.

13. The composition of claim 12 wherein said steroid is estradiol and said protein is steroid free bovine serum albumin.

14. The composition of claim 13 wherein said aqueous solution is other than plasma.

15. The composition of claim 11 wherein said diethylenetriamine pentaacetic acid is present in a concentration of greater than about 0.1 mM.

16. The composition of claim 15 wherein said diethylenetriamine pentaacetic acid is present in a concentration between about 0.2 and 50 mM.

17. The composition of claim 7 herein said steroid is present in a concentration between about $2.5 \times 10^{-11}$ and $1.0 \times 10^{-7}$ g/ml.

18. A method for stabilizing aqueous metal-ion containing solutions of steroid immunoassay reference standards comprising the step of adding an effective chelating amount of at least about 0.1 mM of diethylene triamine pentaacetic acid to a steroid in said aqueous solution, wherein said acid sequesters metal ions from said solution.

19. The method of claim 18 wherein the chelating amount of diethylene triamine pentaacetic acid is from about 0.2 mM to 50 mM.

* * * * *